(12) United States Patent
McEneany et al.

(10) Patent No.: US 11,154,635 B2
(45) Date of Patent: Oct. 26, 2021

(54) POROUS POLYESTER MATERIAL

(71) Applicant: Kimberly-Clark Worldwide, Inc., Neenah, WI (US)

(72) Inventors: Ryan J. McEneany, Appleton, WI (US); Yuewen Xu, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 4 days.

(21) Appl. No.: 16/470,821

(22) PCT Filed: Jan. 19, 2018

(86) PCT No.: PCT/US2018/014398
§ 371 (c)(1),
(2) Date: Jun. 18, 2019

(87) PCT Pub. No.: WO2018/144241
PCT Pub. Date: Aug. 9, 2018

(65) Prior Publication Data
US 2019/0343978 A1    Nov. 14, 2019

Related U.S. Application Data

(60) Provisional application No. 62/452,569, filed on Jan. 31, 2017.

(51) Int. Cl.
| | | |
|---|---|---|
| C08L 67/04 | (2006.01) | |
| A61L 15/26 | (2006.01) | |
| C08J 9/00 | (2006.01) | |
| A61F 13/531 | (2006.01) | |
| A61L 15/42 | (2006.01) | |
| B32B 5/02 | (2006.01) | |
| B32B 5/18 | (2006.01) | |
| D01F 8/14 | (2006.01) | |
| D04H 3/011 | (2012.01) | |
| C08L 67/02 | (2006.01) | |
| D04H 1/4382 | (2012.01) | |
| A61F 13/53 | (2006.01) | |

(52) U.S. Cl.
CPC ............ *A61L 15/26* (2013.01); *A61F 13/531* (2013.01); *A61L 15/425* (2013.01); *B32B 5/022* (2013.01); *B32B 5/18* (2013.01); *C08J 9/0061* (2013.01); *C08L 67/02* (2013.01); *C08L 67/025* (2013.01); *C08L 67/04* (2013.01); *D01F 8/14* (2013.01); *D04H 1/43828* (2020.05); *D04H 3/011* (2013.01); *A61F 2013/530233* (2013.01); *B32B 2262/0276* (2013.01); *B32B 2266/0264* (2013.01); *B32B 2555/02* (2013.01); *C08J 2367/03* (2013.01); *C08J 2400/26* (2013.01); *D04H 1/4383* (2020.05); *D04H 1/43832* (2020.05); *Y10T 428/24479* (2015.01); *Y10T 428/249953* (2015.04)

(58) Field of Classification Search
CPC ...... A61L 15/26; A61L 15/425; C08J 9/0061; C08J 2367/03; C08J 2400/26; C08L 67/025; C08L 67/04; C08L 67/02; A61F 13/531; A61F 2013/530233; A61F 31/06; A61F 31/146; A61F 2013/21028; A61F 13/51; A61F 13/511; A61F 13/514; A61F 13/15; B32B 5/022; B32B 5/18; B32B 2262/0276; B32B 2266/0264; B32B 2555/02; D01F 8/14; D04H 3/011; D04H 3/005; D04H 1/4382; Y10T 428/249953; Y10T 428/24479
See application file for complete search history.

(56) References Cited

U.S. PATENT DOCUMENTS

| | | | |
|---|---|---|---|
| 5,192,308 A | 3/1993 | Ostapchenko | |
| 5,354,532 A | 10/1994 | Nakai et al. | |
| 6,548,431 B1 | 4/2003 | Bansal et al. | |
| 8,110,609 B2 | 2/2012 | Determan et al. | |
| 2005/0260911 A1 | 11/2005 | Ochi et al. | |
| 2008/0125551 A1* | 5/2008 | Vollenberg ............ C08L 67/025 525/439 |
| 2012/0231690 A1 | 9/2012 | Pourdeyhimi et al. | |
| 2013/0210308 A1 | 8/2013 | McEneany et al. | |
| 2015/0318067 A1 | 11/2015 | Asano et al. | |
| 2016/0177048 A1 | 6/2016 | Topolkaraev et al. | |

FOREIGN PATENT DOCUMENTS

| | | | | |
|---|---|---|---|---|
| CN | 101563392 A | 10/2009 | | |
| CN | 102143996 A | 8/2011 | | |
| CN | 103981635 | 8/2014 | | |
| KR | 1020020061648 | 7/2002 | | |
| RU | 2279267 C2 | 7/2006 | | |
| RU | 2280047 C2 | 7/2006 | | |
| RU | 2561122 C2 | 8/2015 | | |
| RU | 2588235 C2 | 6/2016 | | |
| RU | 2605179 C1 | 12/2016 | | |
| WO | WO2014199269 | 12/2014 | | |
| WO | WO-2014199275 A1 * | 12/2014 | ............ B29C 55/18 |
| WO | WO-2015019201 A1 * | 2/2015 | ............ C08L 23/16 |

(Continued)

OTHER PUBLICATIONS

International Search Report and Opinion for PCT/US2018/014398 dated Jun. 29, 2018, 13 pages.

(Continued)

*Primary Examiner* — Kara B Boyle

(74) *Attorney, Agent, or Firm* — Dority & Manning, P.A.

(57) ABSTRACT

A polymeric material that includes a thermoplastic composition containing a continuous phase that includes a polyester and a copolyetherester elastomer is provided. The copolyetherester elastomer is dispersed within the continuous phase in the form of discrete domains. A porous network is defined within the thermoplastic composition that includes a plurality of nanopores.

26 Claims, 5 Drawing Sheets

(56) References Cited

FOREIGN PATENT DOCUMENTS

WO     WO2016/085711 A1     6/2016
WO     WO2016100057     6/2016

OTHER PUBLICATIONS

International Preliminary Report on Patentability for PCT/US2018/014398, dated Dec. 18, 2018, 4 pages.
Russian Office Action Corresponding to Application No. 20191223619 dated Apr. 27, 2021.
Chinese Office Action Corresponding to Application No. 20180006746 dated Apr. 3, 2021.

* cited by examiner

POROUS POLYESTER MATERIAL

RELATED APPLICATIONS

The present application is the national stage entry of International Patent Application No. PCT/US2018/014398 having a filing date of Jan. 19, 2018, which claims priority to U.S. provisional application Ser. No. 62/452,569, filed on Jan. 31, 2017, which are incorporated herein in their entirety by reference thereto.

BACKGROUND OF THE INVENTION

Significant efforts have been made to produce low density polymeric materials to improve the use of natural resources and reduction of the carbon footprint in finished products. A typical approach to producing such low density materials is by foaming the polymer using physical or chemical blowing agents, which create gas-filled pores though the bulk. Chemical blowing agents are compounds that undergo chemical reaction liberating gas that creates the pore structure through the bulk of the polymer. Physical blowing agents are typically compressed gases that are dispersed in the polymer and expand creating the pores. Regardless, typical foaming processes induce low molecular orientation because the pore formation happens when the polymer is in the molten state. This prevents the polymer from strain hardening, which typically occurs at temperatures well above the melting temperature or glass transition temperature of the polymer, yielding products with low mechanical strength. Furthermore, typical foaming processes generate large cell sizes, such as greater than 100 µm. This reduces the melt strength, thus leading to breaks in high speed production processes with high deformation rates (e.g., fiber spinning, film formation, molding, etc.).

As such, a need currently exists for an improved polymeric material that is porous.

SUMMARY OF THE INVENTION

In accordance with one embodiment of the present invention, a polymeric material (e.g., fiber, film, molded article, etc.) is disclosed that comprises a thermoplastic composition. The composition contains a continuous phase that includes a polyester and a copolyetherester elastomer. The copolyetherester elastomer is dispersed within the continuous phase in the form of discrete domains. A porous network is defined within the thermoplastic composition that includes a plurality of nanopores.

In accordance with another embodiment of the present invention, a method method for forming a polymeric material is disclosed that comprises forming a thermoplastic composition that contains a continuous phase that includes a polyester and a copolyetherester elastomer that is dispersed within the continuous phase in the form of discrete domains; and solid state drawing the thermoplastic composition to form a porous network therein, the porous network including a plurality of nanopores.

In accordance with yet another embodiment of the present invention, a method for forming a fiber is disclosed that comprises forming a thermoplastic composition that contains a continuous phase that includes a polyester and a copolyetherester elastomer that is dispersed within the continuous phase in the form of discrete domains; extruding the composition through a capillary to form the fiber; and drawing the fiber at a temperature that is lower than the melting temperature of the polyester, thereby forming a porous network that includes a plurality of nanopores.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
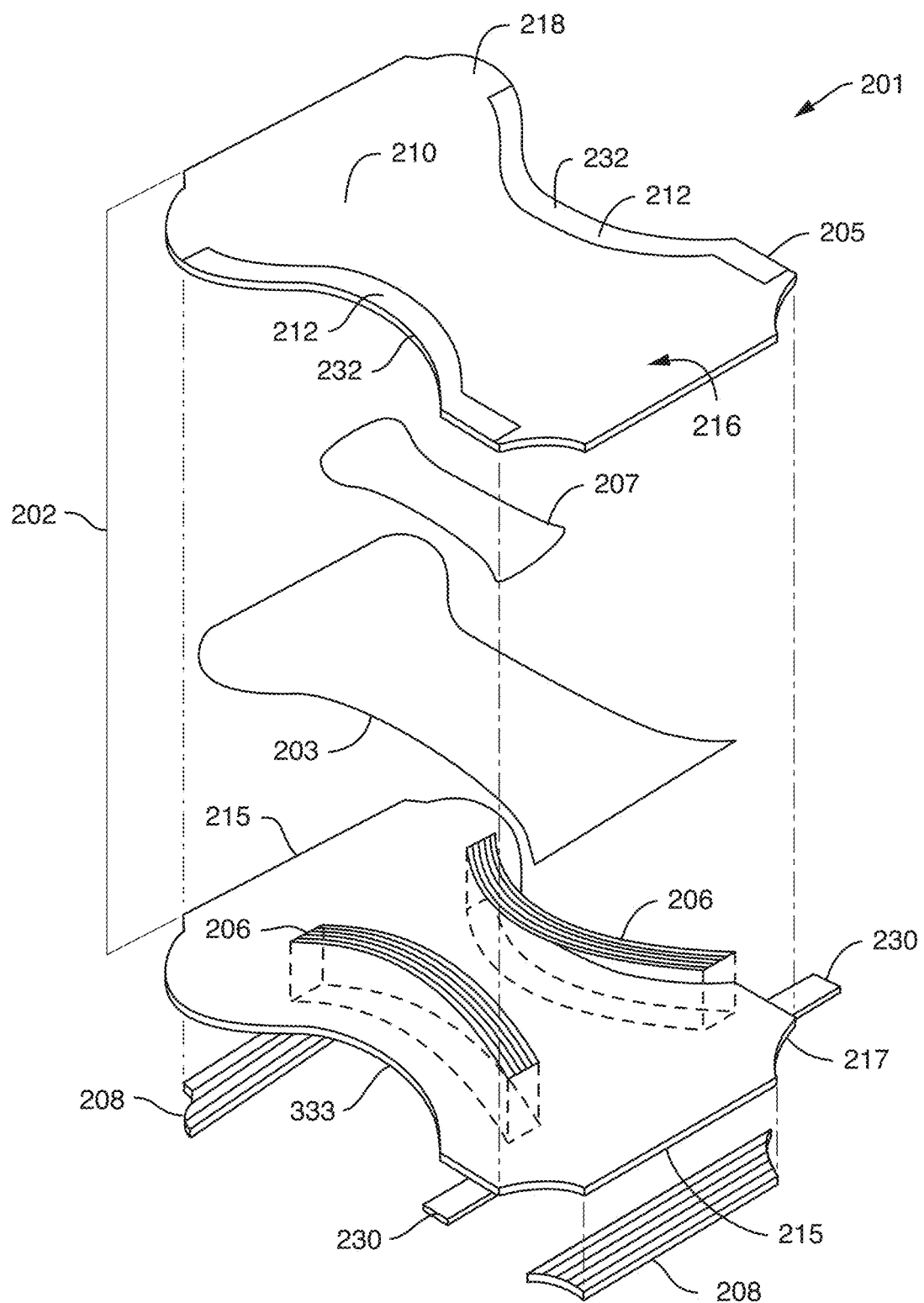
FIG. 1 is a perspective view of one embodiment of an absorbent article that can employ the polymeric material of the present invention.

Repeat use of references characters in the present specification and drawings is intended to represent same or analogous features or elements of the invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a polymeric material (e.g., film, fibrous material, molded article, etc.) that is formed by drawing of a thermoplastic composition (e.g., solid state drawing) containing a continuous phase that includes a polyester and a copolyetherester elastomer. Due to its molecular weight and viscosity, the elastomer can become dispersed within the continuous phase as discrete nano-scale phase domains. Further, the copolyetherester elastomer generally contains multiple hard and soft segments. The presence of hard segments within the elastomer can help facilitate the formation of domains, while the presence of soft segments can enhance flexibility and also facilitate debonding during pore formation.

In this regard, when the composition is subjected to a deformation and elongational strain (e.g., during drawing), the present inventors have discovered that the nano-scale phase domains formed by the copolyetherester elastomer are able to interact in a unique manner to create a network of pores. Namely, it is believed that elongational strain can initiate intensive localized shear zones and/or stress intensity zones (e.g., normal stresses) near the discrete phase domains as a result of stress concentrations that arise from the incompatibility of the copolyetherester elastomer and the polyester. These shear and/or stress intensity zones cause some initial debonding in the polyester adjacent to the domains. Once initial pores are formed, the polyester located between domains can deform plastically to create internal stretched areas that locally narrow (or neck) and strain-harden. This process allows the formation of pores through the bulk of the composition that grow in the stretching direction, thereby leading to the formation of a porous network while the molecular orientation leads to strain-hardening that enhances mechanical strength. Further, due to the flexibility of the copolyetherester elastomer, the pores can also become distributed in a more homogeneous fashion throughout the composition.

Through the techniques noted above, a stable porous network may be formed in the polymeric material so that the average percent volume occupied by the pores within a given unit volume of the material may be from about 15% to about 80% per cm$^3$, in some embodiments from about 20% to about 70%, and in some embodiments, from about 30% to about 60% per cubic centimeter of the material. With such a pore volume, the composition may have a relatively low density, such as about 1.3 g/cm$^3$ or less, in some embodiments from about 0.4 to about 1.1 g/cm$^3$, and in some embodiments, from about 0.5 to about 0.9 g/cm$^3$. A substantial portion of pores in the porous network are also of a "nano-scale" size ("nanopores"), such as those having an average cross-sectional dimension of about 800 nanometers or less, in some embodiments from about 5 to about 700 nanometers, and in some embodiments, from about 10 to about 500 nanometers. The term "cross-sectional dimension" generally refers to a characteristic dimension (e.g., width or diameter) of a pore, which is substantially orthogonal to its major axis (e.g., length) and also typically substantially orthogonal to the direction of the stress applied during drawing. The nanopores may also have an average axial dimension within the range of from about 100 to about 5000 nanometers, in some embodiments from about 50 to about 2000 nanometers, and in some embodiments, from about 100 to about 1000 nanometers. The "axial dimension" is the dimension in the direction of the major axis (e.g., length), which is typically in the direction of drawing. Such nanopores may, for example, constitute about 15 vol. % or more, in some embodiments about 20 vol. % or more, in some embodiments from about 30 vol. % to 100 vol. %, and in some embodiments, from about 40 vol. % to about 90 vol. % of the total pore volume in the polymeric material.

Various embodiments of the present invention will now be described in more detail.

I. Thermoplastic Composition

A. Polyester

As indicated above, the thermoplastic composition contains a continuous phase within which a copolyetherester elastomer is dispersed. The continuous phase contains one or more polyesters and typically constitutes from about 60 wt. % to about 99 wt. %, in some embodiments from about 75 wt. % to about 98 wt. %, and in some embodiments, from about 80 wt. % to about 95 wt. % of the thermoplastic composition. Any of a variety of polyesters may be employed in the continuous phase, such as aliphatic polyesters, such as polycaprolactone, polyesteramides, polylactic acid (PLA) and its copolymers, polyglycolic acid, polyalkylene carbonates (e.g., polyethylene carbonate), poly-3-hydroxybutyrate (PHB), poly-3-hydroxyvalerate (PHV), poly-3-hydroxybutyrate-co-4-hydroybutyrate, poly-3-hydroxybutyrate-co-3-hydroxyvalerate copolymers (PHBV), poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate-based aliphatic polymers (e.g., polybutylene succinate, polybutylene succinate adipate, polyethylene succinate, etc.); aliphatic-aromatic copolyesters (e.g., polybutylene adipate terephthalate, polyethylene adipate terephthalate, polyethylene adipate isophthalate, polybutylene adipate isophthalate, etc.); aromatic polyesters (e.g., polyethylene terephthalate, polybutylene terephthalate, etc.); and so forth.

In certain cases, the thermoplastic composition may contain at least one polyester that is rigid in nature, such as polyethylene terephthalate or polylactic acid, and thus has a relatively high glass transition temperature. For example, the glass transition temperature ("$T_g$") may be about 0° C. or more, in some embodiments from about 5° C. to about 120° C., in some embodiments from about 30° C. to about 110° C., and in some embodiments, from about 50° C. to about 100° C. The polyester may also have a melting temperature of from about 140° C. to about 320° C., in some embodiments from about 150° C. to about 300° C., and in some embodiments, from about 200° C. to about 275° C. The melting temperature may be determined using DSC in accordance with ASTM D3417-99. The glass transition temperature may be determined by dynamic mechanical analysis in accordance with ASTM E1640-09. When employed, the rigid polyester typically has a number average molecular weight ("$M_n$") ranging from about 40,000 to about 180,000 grams per mole, in some embodiments from about 50,000 to about 160,000 grams per mole, and in some embodiments, from about 80,000 to about 120,000 grams per mole. Likewise, the polymer also typically has a weight average molecular weight ("$M_w$") ranging from about 80,000 to about 250,000 grams per mole, in some embodiments from about 100,000 to about 200,000 grams per mole, and in some embodiments, from about 110,000 to about 160,000 grams per mole. The ratio of the weight average molecular weight to the number average molecular weight ("$M_w/M_n$"), i.e., the "polydispersity index", is also relatively low. For example, the polydispersity index typically ranges from about 1.0 to about 3.0, in some embodiments from about 1.1 to about 2.0, and in some embodiments, from about 1.2 to about 1.8. The weight and number average molecular weights may be determined by methods known to those skilled in the art. The polyester may also have an intrinsic viscosity of from about 0.2 to about 1.5 deciliters per gram (dL/g), in some embodiments from about 0.4 to about 1.2 dL/g, and in some embodiments, from about 0.5 to about 0.9 dL/g.

Some types of neat polyesters (e.g., polylactic acid) can absorb water from the ambient environment such that it has a moisture content of about 500 to 600 parts per million ("ppm"), or even greater, based on the dry weight of the starting polyester. Moisture content may be determined in a variety of ways as is known in the art, such as in accordance with ASTM D7191-10, such as described below. Because the presence of water during melt processing can hydrolytically degrade the polyester and reduce its molecular weight, it is sometimes desired to dry the polyester prior to blending. In most embodiments, for example, it is desired that the polyester have a moisture content of about 300 parts per million ("ppm") or less, in some embodiments about 200 ppm or less, in some embodiments from about 1 to about 100 ppm prior to blending with the copolyetherester elastomer. Drying of the polyester may occur, for instance, at a temperature of from about 50° C. to about 160° C., and in some embodiments, from about 100° C. to about 150° C.

B. Copolyetherester Elastomer

A thermoplastic copolyetherester elastomer is also employed in the composition. Without intending to be limited by theory, it is believed that the copolyetherester elastomer is at least partially incompatible with the polyester polymer in the sense that it can be substantially uniformly distributed within the polyester, but in the form of discrete domains. Prior to drawing, the discrete domains may be of a nano-scale size, such as having an average cross-sectional dimension of from about 1 to about 1000 nanometers, in some embodiments from about 5 to about 800 nanometers, in some embodiments from about 10 to about 500 nanometers, and in some embodiments from about 20 to about 200 nanometers. The domains may have a variety of different shapes, such as elliptical, spherical, cylindrical, plate-like, tubular, etc. In one embodiment, for example, the domains have a substantially elliptical shape. The copolyetherester elastomer is typically employed in an amount of from about 0.05 wt. % to about 20 wt. %, in some embodiments from about 0.1 wt. % to about 10 wt. %, and in some embodiments, from about 0.5 wt. % to about 8 wt. %, based on the weight of the continuous phase. The concentration of the copolyetherester elastomer in the entire thermoplastic composition may likewise be from about 0.01 wt. % to about 15 wt. %, in some embodiments from about 0.05 wt. % to about 10 wt. %, and in some embodiments, from about 0.3 wt. % to about 6 wt. % of the thermoplastic composition.

Any of a variety of thermoplastic copolyetherester elastomers may generally be employed in the present invention. Typically, such elastomers are segmented block copolymers that have recurring "long chain ester units" and "short chain ester units" joined through ester linkages. The long chain units can be represented by the formula:

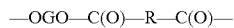

and the short chain ester units are represented by the structure:

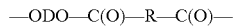

wherein,

G is a divalent group that is derived from one or more high molecular weight alcohols (e.g., polymeric glycol);

R is a hydrocarbon group derived from one or more dicarboxylic acids (e.g., terephthalic acid, isophthalic acid, etc.); and D is a divalent group derived from one or more low molecular weight diols (e.g., 1,4-butane diol, ethylene glycol, etc.).

The "long chain units" are typically formed from the reaction product of a high molecular weight alcohol with a dicarboxylic acid and the "short chain ester units" are typically formed from the reaction of a low molecular weight diol with a dicarboxylic acid. The high molecular weight alcohol may, for instance, have a number average molecular weight of about 400 grams per mole or more, and in some embodiments, from about 600 to about 10,000 grams per mole. Examples of such alcohols include, for instance, polymeric glycols having terminal hydroxy groups, and particularly those derived from 1,2-alkylene oxides containing 2 to about 10 carbon atoms (e.g., ethylene oxide, 1,2-propylene oxide, 1,2-butylene oxide and 1,2-hexylene oxide). In one embodiment, for instance, the high molecular weight alcohol is a random or block copolymer of ethylene oxide and 1,2-propylene oxide. In another embodiment, the high molecular weight alcohol is a poly(oxytetramethylene)glycols derived from tetrahydrofuran. The low molecular weight diols may have a number average molecular weight of less than about 400 grams per mole and in some embodiments, from about 50 to about 300 grams per mole. Examples of suitable diols include, for instance, ethylene glycol, propylene glycol, 1,4-butanediol, 1,6-hexamethylene glycol, dihydroxycyclohexane, cyclohexane dimethanol, resorcinol, hydroquinone, 1,5-dihydroxynaphthalene, bisphenol A and so forth. Equivalent ester forming derivatives of diols, e.g., ethylene oxide or propylene carbonate, may also be employed. Further, if desired, a mixture of high molecular weight alcohols and/or low molecular weight diols may also be employed. Thus, for example, the letter "G" in the formula above may represent the residue of a single long chain glycol or the residue of several different glycols and/or the letter "D" may represent the residue of one or several low molecular weight diols.

The term "dicarboxylic acid" as used herein is intended to include the condensation polymerization equivalents of dicarboxylic acids, i.e., their esters or ester forming derivatives, such as acid chlorides, anhydrides, or other derivatives which behave substantially like dicarboxylic acids in a polymerization reaction with a glycol. The dicarboxylic acids may also be aromatic, aliphatic, and/or aliphatic-aromatic in nature. Particularly suitable aromatic dicarboxylic acids may include, for instance, orthophthalic acid, isophthalic acid, terephthalic acid, bibenzoic acid, etc., as well as esters or ester-forming derivatives thereof. Likewise, suitable aliphatic dicarboxylic acids may include succinic acid, glutaric acid, adipic acid, pimelic acid, suberic acid, azelaic acid, sebacic acid, oxalic acid, fumaric acid, etc., as well as esters or ester-forming derivatives thereof. If desired, a mixture of dicarboxylic acids, such as terephthalic acid and isophthalic acid, may also be employed. Thus, the letter "R" in the formula above may also represent the residue of one or several dicarboxylic acids.

Regardless of the particular materials employed, the resulting copolyetherester elastomer is typically formed to have a certain melt viscosity to ensure that the discrete domains and resulting pores can be adequately maintained. For example, if the viscosity of the copolyetherester elastomer is too low (or melt flow rate is too high), it tends to flow and disperse uncontrollably through the continuous phase. This results in lamellar, plate-like domains or co-continuous phase structures that are difficult to maintain and also likely to prematurely fracture. Conversely, if the viscosity is too high (or melt flow rate is too low), it tends to clump together and form very large elliptical domains, which are difficult to disperse during blending. This may cause uneven distribution of the copolyetherester elastomer through the entirety of the continuous phase. The copolyetherester elastomer may thus, for example, have a melt flow rate (on a dry basis) of from about 0.1 to about 100 grams per 10 minutes, in some embodiments from about 0.5 to about 50 grams per 10 minutes, and in some embodiments, from about 5 to about 15 grams per 10 minutes, determined at a load of 2160 grams and at a temperature at least about 40° C. above the melting temperature (e.g., at 190° C.) in accordance with ASTM D1238-13. The polyester may likewise have a melt flow rate (on a dry basis) of from about 0.5 to about 80 grams per 10 minutes, in some embodiments from about 1 to about 40 grams per 10 minutes, and in some embodiments, from about 5 to about 20 grams per 10 minutes, determined at a load of 2160 grams and at a temperature at least about 40° C. above the melting temperature (e.g., 260° C. for certain polyesters) in accordance with ASTM D1238-13.

C. Microinclusion Additive

Although by no means required, the composition of the present invention may also employ a microinclusion additive, such as in an amount of from about 1 wt. % to about 30 wt. %, in some embodiments from about 2 wt. % to about 25 wt. %, and in some embodiments, from about 5 wt. % to about 20 wt. %, based on the weight of the continuous phase employed in the composition. The concentration of the microinclusion additive in the entire thermoplastic composition may likewise constitute from about 0.1 wt. % to about 30 wt. %, in some embodiments from about 0.5 wt. % to about 25 wt. %, and in some embodiments, from about 1 wt. % to about 20 wt. %.

The term "microinclusion additive" generally refers to any material that is capable of being dispersed within the continuous phase in the form of discrete domains of a micro-scale size. For example, prior to drawing, the domains may have an average cross-sectional dimension of from about 0.1 μm to about 25 μm, in some embodiments from about 0.5 μm to about 20 μm, and in some embodiments from about 1 μm to about 10 μm. When employed, the micro-scale and nano-scale phase domains are able to interact in a unique manner when subjected to a deformation and elongational strain (e.g., drawing) to create a network of pores. Namely, it is believed that elongational strain can initiate intensive localized shear zones and/or stress intensity zones (e.g., normal stresses) near the micro-scale discrete phase domains as a result of stress concentrations that arise from the incompatibility of the materials. These shear and/or stress intensity zones cause some initial debonding in the polyester adjacent to the micro-scale domains. Notably, however, the localized shear and/or stress intensity zones created near the nano-scale discrete phase domains may overlap with the micro-scale zones to cause even further debonding to occur in the polyester, thereby creating a substantial number of nanopores adjacent to the nano-scale domains and/or micro-scale domains.

The particular nature of the microinclusion additive is not critical, and may include liquids, semi-solids, or solids (e.g., amorphous, crystalline, or semi-crystalline). In certain embodiments, the microinclusion additive is polymeric in nature and possesses a relatively high molecular weight to help improve the melt strength and stability of the thermoplastic composition. Typically, the microinclusion additive polymer may be generally incompatible with the polyester. In this manner, the additive can better become dispersed as discrete phase domains within a continuous phase of the polyester. The discrete domains are capable of absorbing energy that arises from an external force, which increases the overall toughness and strength of the resulting polymeric material. The domains may have a variety of different shapes, such as elliptical, spherical, cylindrical, plate-like, tubular, etc. In one embodiment, for example, the domains have a substantially elliptical shape. The physical dimension of an individual domain is typically small enough to minimize the propagation of cracks through the material upon the application of an external stress, but large enough to initiate microscopic plastic deformation and allow for shear zones at and around particle inclusions.

As noted above, the microinclusion additive may also have a certain melt flow rate (or viscosity) to ensure that the discrete domains and resulting pores can be adequately maintained. For example, the ratio of the melt flow rate of the microinclusion additive to the melt flow rate of the polyester is typically from about 0.2 to about 8, in some embodiments from about 0.5 to about 6, and in some embodiments from about 1 to about 5. The microinclusion additive may, for example, have a melt flow rate of from about 0.1 to about 250 grams per 10 minutes, in some embodiments from about 0.5 to about 200 grams per 10 minutes, and in some embodiments, from about 5 to about 150 grams per 10 minutes, determined at a load of 2160 grams and at a temperature at least about 40° C. above its melting temperature (e.g., 120° C. to 180° C.).

In addition to the properties noted above, the mechanical characteristics of the microinclusion additive may also be selected to achieve the desired porous network. For example, when a blend of the polyester and microinclusion additive is applied with an external force, stress concentrations (e.g., including normal or shear stresses) and shear and/or plastic yielding zones may be initiated at and around the discrete phase domains as a result of stress concentrations that arise from a difference in the elastic modulus of the additive and polyester. Larger stress concentrations promote more intensive localized plastic flow at the domains, which allows them to become significantly elongated when stresses are imparted. These elongated domains can allow the composition to exhibit a more pliable and softer behavior than the polyester, such as when it is a rigid polyester resin (e.g., polyethylene terephthalate). To enhance the stress concentrations, the microinclusion additive may be selected to have a relatively low Young's modulus of elasticity in comparison to the polyester. For example, the ratio of the modulus of elasticity of the polyester to that of the additive is typically from about 1 to about 250, in some embodiments from about 2 to about 100, and in some embodiments, from about 2 to about 50. The modulus of elasticity of the microinclusion additive may, for instance, range from about 2 to about 1000 Megapascals (MPa), in some embodiments from about 5 to about 500 MPa, and in some embodiments, from about 10 to about 200 MPa. To the contrary, the modulus of elasticity of polylactic acid, for example, is typically from about 800 MPa to about 3000 MPa.

While a wide variety of microinclusion additives may be employed that have the properties identified above, particularly suitable examples of such additives may include synthetic polymers, such as polyolefins (e.g., polyethylene, polypropylene, polybutylene, etc.); styrenic copolymers (e.g., styrene-butadiene-styrene, styrene-isoprene-styrene, styrene-ethylene-propylene-styrene, styrene-ethylene-butadiene-styrene, etc.); polytetrafluoroethylenes; polyesters (e.g., recycled polyester, polyethylene terephthalate, etc.); polyvinyl acetates (e.g., poly(ethylene vinyl acetate), polyvinyl chloride acetate, etc.); polyvinyl alcohols (e.g., polyvinyl alcohol, poly(ethylene vinyl alcohol), etc.); polyvinyl butyrals; acrylic resins (e.g., polyacrylate, polymethylacrylate, polymethylmethacrylate, etc.); polyamides (e.g., nylon); polyvinyl chlorides; polyvinylidene chlorides; polystyrenes; polyurethanes; etc. Suitable polyolefins may, for instance, include ethylene polymers (e.g., LDPE, HDPE, LLDPE, etc.), propylene homopolymers (e.g., syndiotactic, atactic, isotactic, etc.), propylene copolymers, and so forth.

D. Other Components

Other suitable materials that may also be used in the thermoplastic composition, such as lubricants, compatibilizers, catalysts, antioxidants, stabilizers, surfactants, waxes, solid solvents, nucleating agents, particulates, nanofillers, and other materials added to enhance the processability and mechanical properties of the thermoplastic composition. Nevertheless, one beneficial aspect of the present invention is that good properties may be provided without the need for various conventional additives, such as blowing agents (e.g., chlorofluorocarbons, hydrochlorofluorocarbons, hydrocarbons, carbon dioxide, supercritical carbon dioxide, nitrogen, etc.), pore-initiating fillers (e.g., calcium carbonate), and hydrophobic interphase modifiers (e.g., polyether polyol). In fact, the thermoplastic composition may be generally free of blowing agents, pore-initiating fillers, and/or interphase modifiers. For example, such blowing agents, fillers, and/or interphase modifiers may be present in an amount of no more than about 1 wt. %, in some embodiments no more than about 0.5 wt. %, and in some embodiments, from about 0.001 wt. % to about 0.2 wt. % of the thermoplastic composition. Further, due to its stress whitening properties, as described in more detail below, the resulting composition may achieve an opaque color (e.g., white) without the need for conventional pigments, such as titanium dioxide. In certain embodiments, for example, pigments may be present in an amount of no more than about 1 wt. %, in some embodiments no more than about 0.5 wt. %, and in some embodiments, from about 0.001 wt. % to about 0.2 wt. % of the thermoplastic composition.

II. Polymeric Material

The polymeric material may generally be formed by drawing the thermoplastic composition. To form the initial thermoplastic composition, the components are typically blended together using any of a variety of known techniques. In one embodiment, for example, the components may be supplied separately or in combination. For instance, the components may first be dry mixed together to form an essentially homogeneous dry mixture, and they may likewise be supplied either simultaneously or in sequence to a melt processing device that dispersively blends the materials. Batch and/or continuous melt processing techniques may be employed. For example, a mixer/kneader, Banbury mixer, Farrel continuous mixer, single-screw extruder, twin-screw extruder, roll mill, etc., may be utilized to blend and melt process the materials. Particularly suitable melt processing devices may be a co-rotating, twin-screw extruder (e.g., ZSK-30 extruder available from Werner & Pfleiderer Corporation of Ramsey, N.J. or a Thermo Prism™ USALAB 16 extruder available from Thermo Electron Corp., Stone, England). Such extruders may include feeding and venting ports and provide high intensity distributive and dispersive mixing. For example, the components may be fed to the same or different feeding ports of the twin-screw extruder and melt blended to form a substantially homogeneous melted mixture. If desired, other additives may also be injected into the polymer melt and/or separately fed into the extruder at a different point along its length.

Regardless of the particular processing technique chosen, the resulting melt blended composition typically contains nano-scale domains of the nanoinclusion additive and optionally micro-scale domains of the microinclusion additive. The degree of shear/pressure and heat may be controlled to ensure sufficient dispersion, but not so high as to adversely reduce the size of the domains so that they are incapable of achieving the desired properties. For example, blending typically occurs at a temperature of from about 180° C. to about 330° C., in some embodiments from about 185° C. to about 310° C., and in some embodiments, from about 190° C. to about 290° C. Likewise, the apparent shear rate during melt processing may range from about 10 seconds$^{-1}$ to about 3000 seconds$^{-1}$, in some embodiments from about 50 seconds$^{-1}$ to about 2000 seconds$^{-1}$, and in some embodiments, from about 100 seconds$^{-1}$ to about 1200 seconds$^{-1}$. The apparent shear rate may be equal to $4Q/\pi R^3$, where Q is the volumetric flow rate ("m$^3$/s") of the polymer melt and R is the radius ("m") of the capillary (e.g., extruder die) through which the melted polymer flows. Of course, other variables, such as the residence time during melt processing, which is inversely proportional to throughput rate, may also be controlled to achieve the desired degree of homogeneity.

To achieve the desired shear conditions (e.g., rate, residence time, shear rate, melt processing temperature, etc.), the speed of the extruder screw(s) may be selected with a certain range. Generally, an increase in product temperature is observed with increasing screw speed due to the additional mechanical energy input into the system. For example, the screw speed may range from about 50 to about 600 revolutions per minute ("rpm"), in some embodiments from about 70 to about 500 rpm, and in some embodiments, from about 100 to about 300 rpm. This may result in a temperature that is sufficiently high to disperse or distribute the copolyetherester elastomer without adversely impacting the size of the resulting domains. The melt shear rate, and in turn the degree to which the additives are dispersed, may also be increased through the use of one or more distributive and/or dispersive mixing elements within the mixing section of the extruder. Suitable distributive mixers for single screw extruders may include, for instance, Saxon, Dulmage, Cavity Transfer mixers, etc. Likewise, suitable dispersive mixers may include Blister ring, Leroy/Maddock, CRD mixers, etc. As is well known in the art, the mixing may be further improved by using pins in the barrel that create a folding and reorientation of the polymer melt, such as those used in Buss Kneader extruders, Cavity Transfer mixers, and Vortex Intermeshing Pin (VIP) mixers.

The material may be drawn in-line or after formation to form a stable porous network. Typically, drawing occurs in a "solid state" in the longitudinal direction (e.g., machine direction), transverse direction (e.g., cross-machine direction), etc., as well as combinations thereof. By "solid state" drawing, it is generally meant that the composition is kept at a temperature below the melting temperature of the polyester. Among other things, this helps to ensure that the polymer chains are not altered to such an extent that the porous network becomes unstable. For example, the composition may be drawn at a temperature of from about −50° C. to about 150° C., in some embodiments from about −40° C. to about 100° C., in some embodiments from about −20° C. to about 90° C., and in some embodiments, from about 20° C. to about 80° C. In certain cases, the drawing temperature may optionally be at least about 10° C., in some embodiments at least about 20° C., and in some embodiments, at least about 30° C. below the glass transition temperature of the component having the highest glass transition temperature (e.g., polyester, copolyetherester elastomer, microinclusion additive, etc.).

To perform the desired drawing, the thermoplastic composition may be formed into a precursor shape, drawn, and thereafter converted into the desired material (e.g., film, fiber, molded article, etc.). In one embodiment, the precursor shape may be a film having a thickness of from about 1 to about 5000 micrometers, in some embodiments from about 2 to about 4000 micrometers, in some embodiments from about 5 to about 2500 micrometers, and in some embodiments, from about 8 to about 500 micrometers. As an alternative to forming a precursor shape, the thermoplastic composition may also be drawn in situ as it is being shaped into the desired form for the polymeric material. In one embodiment, for example, the thermoplastic composition may be drawn as it is being formed into a film or fiber.

Regardless, various drawing techniques may be employed, such as aspiration (e.g., fiber draw units), tensile frame drawing, biaxial drawing, multi-axial drawing, profile drawing, vacuum drawing, etc. In one embodiment, for example, the composition may be in the form of a film that is drawn with a machine direction orienteer ("MDO"), such as commercially available from Marshall and Willams, Co.

of Providence, R.I. MDO units typically have a plurality of drawing rolls (e.g., from 5 to 8) which progressively draw and thin the film in the machine direction. The composition may be drawn in either single or multiple discrete drawing operations. It should be noted that some of the rolls in an MDO apparatus may not be operating at progressively higher speeds. To draw the composition in the manner described above, it is typically desired that the rolls of the MDO are not heated or heated below the glass transition temperature of the polyester in the continuous phase.

In other embodiments, the composition may be in the form of a fiber that is drawn to form the desired porous network. As used herein, the term "fiber" generally refers to an elongated extrudate formed by passing a polymer through a forming orifice, such as a die. Unless noted otherwise, the term "fiber" includes both discontinuous fibers having a definite length and substantially continuous filaments. Substantially filaments may, for instance, have a length much greater than their diameter, such as a length to diameter ratio ("aspect ratio") greater than about 15,000 to 1, and in some cases, greater than about 50,000 to 1. In one embodiment, the fibers may have an average diameter of from about 1 to about 100 micrometers, in some embodiments from about 2 to about 30 micrometers, and in some embodiments, from about 4 to about 15 micrometers.

Fibers formed from the thermoplastic composition may generally have any desired configuration, including monocomponent and multicomponent (e.g., sheath-core configuration, side-by-side configuration, segmented pie configuration, island-in-the-sea configuration, and so forth). Hollow fibers (monocomponent and/or multicomponent) may also be employed, such as described in U.S. Pat. No. 6,642,429 to Carter, et al. In some embodiments, the fibers may contain one or more additional polymers as a component (e.g., bicomponent) or constituent (e.g., biconstituent) to further enhance strength, processibility, and/or other properties. For instance, the thermoplastic composition may form a core component of a sheath/core bicomponent fiber, while an additional polymer may form the sheath component, or vice versa. The additional polymer may be any polymer desired, such as polyesters, e.g., polylactic acid, polyethylene terephthalate, etc.; polyolefins, e.g., polyethylene, polypropylene, polybutylene, and so forth; polytetrafluoroethylene; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; and polyurethanes.

Figure 2:
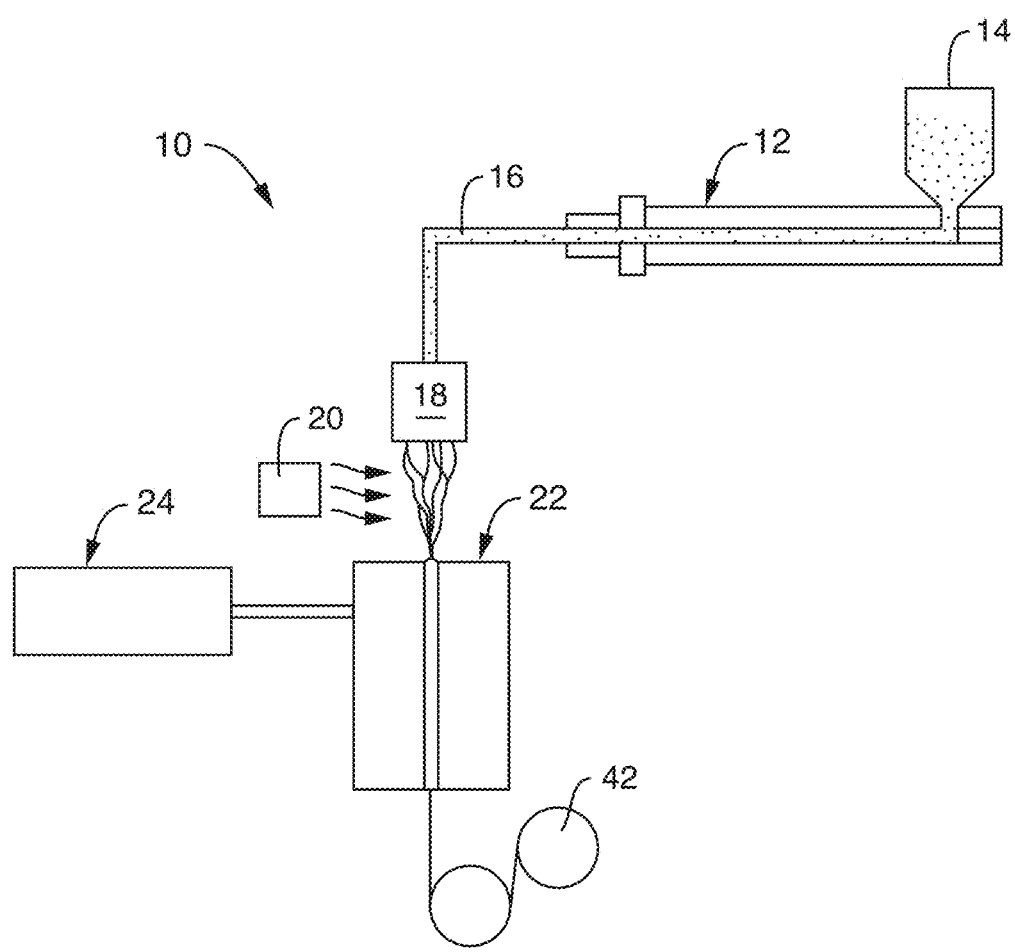
FIG. 2 is a schematic illustration of a process that may be used in one embodiment of the present invention to form a polymeric material.
Figure 3:
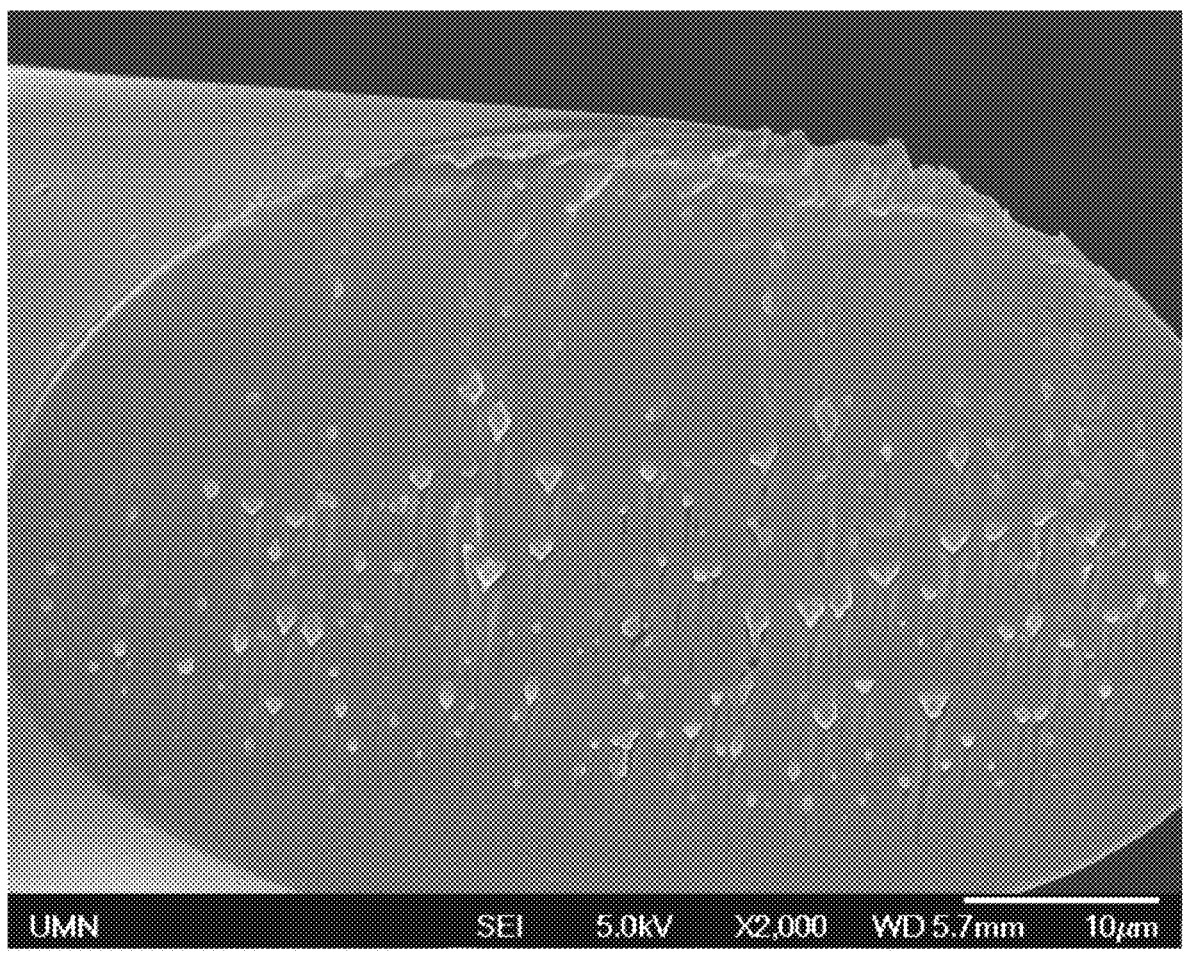
FIG. 3 is an SEM microphotograph of the fiber sample of Example 2.
Figure 4:
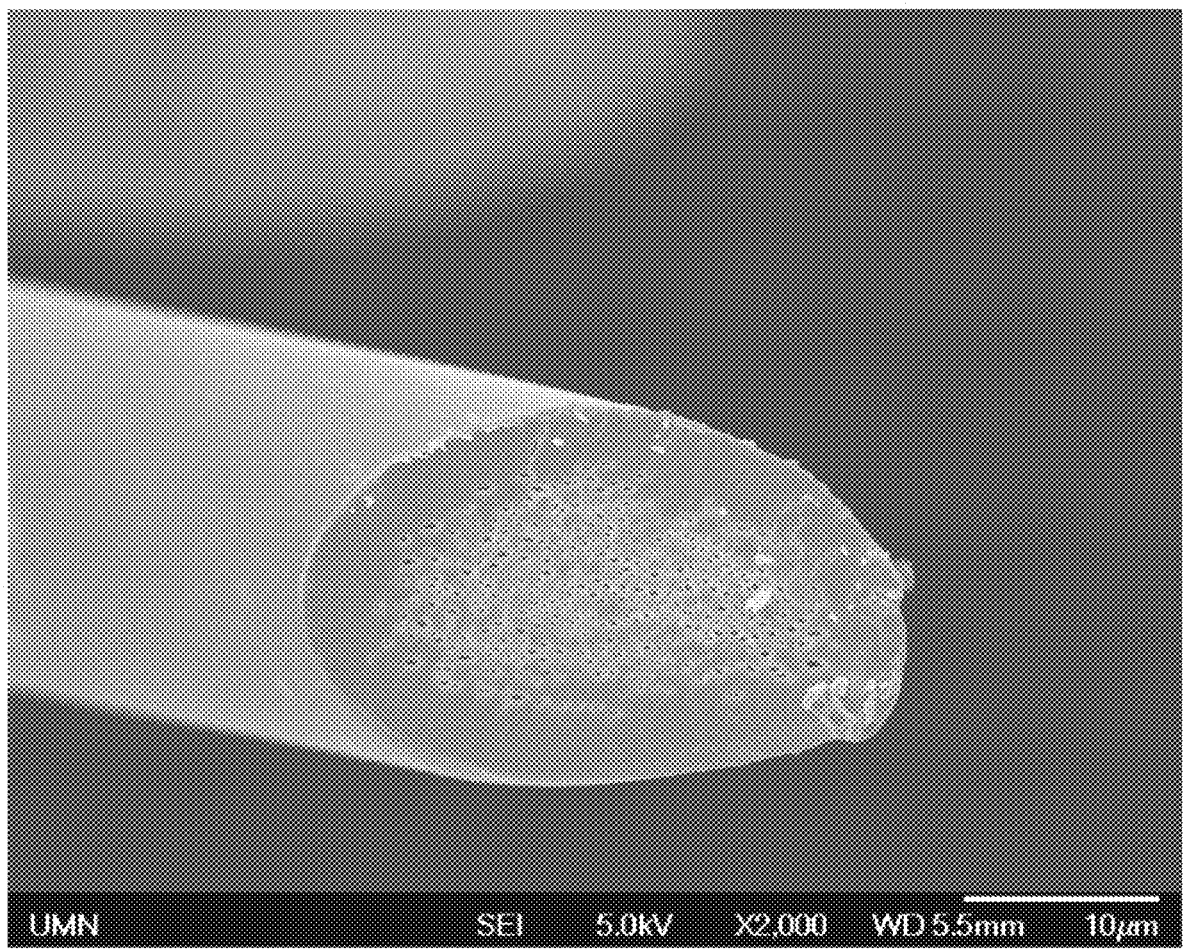
FIGS. 4-5 are SEM microphotographs of the fiber samples of Example 3.
Figure 5:
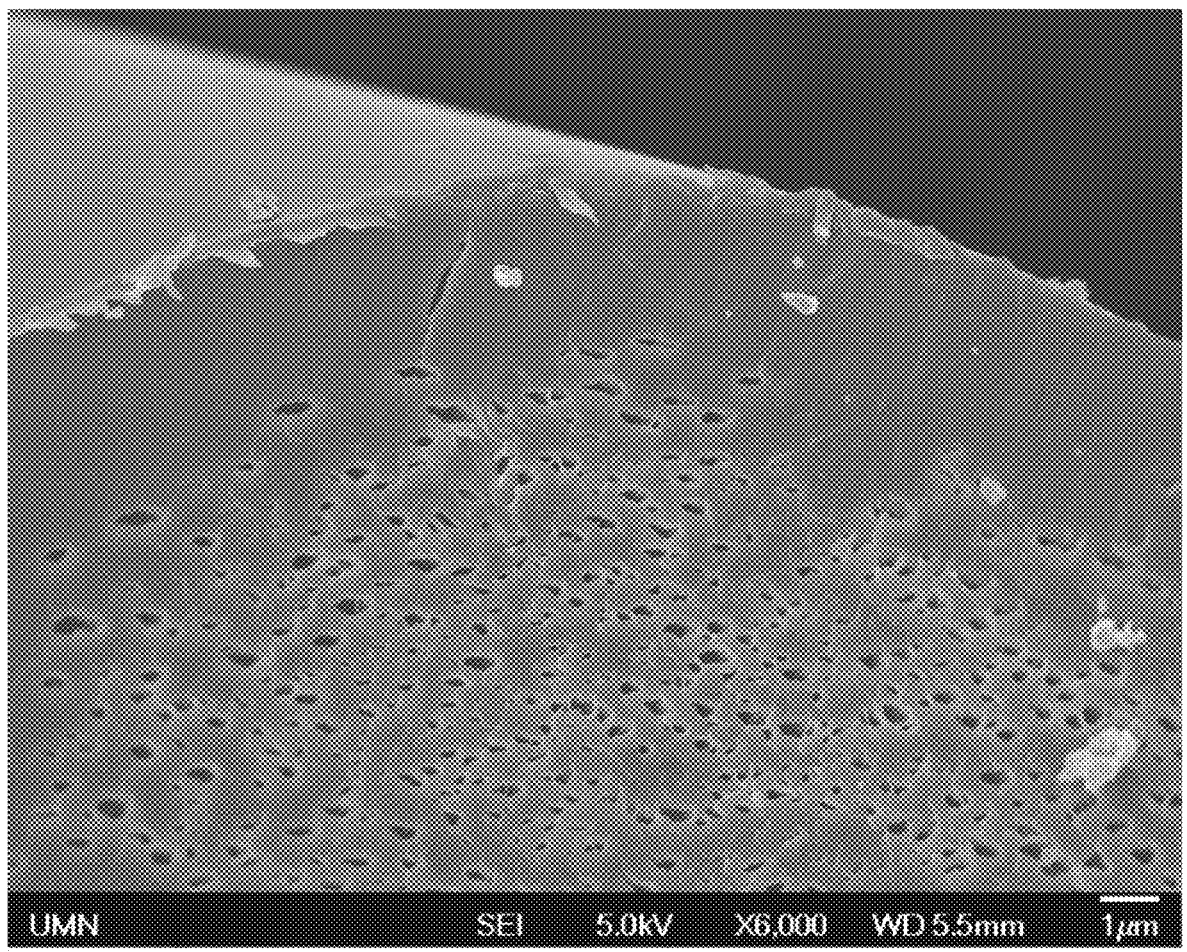

Any of a variety of processes may be used to form the fibers. For example, the thermoplastic composition described above may be extruded through a spinneret and quenched. Referring to FIG. 2, for example, one embodiment of a method for forming fibers is shown in more detail. In this particular embodiment, the thermoplastic composition may be fed into an extruder 12 from a hopper 14. The blend may be provided to the hopper 14 using any conventional technique. The extruder 12 is heated to a temperature sufficient to extrude the melted polymer. The extruded composition is then passed through a polymer conduit 16 to a spinneret 18. For example, the spinneret 18 may include a housing containing a spin pack having a plurality of plates stacked one on top of each other and having a pattern of openings arranged to create flow paths for directing polymer components. The spinneret 18 also has openings arranged in one or more rows. The openings form a downwardly extruding curtain of filaments when the polymers are extruded therethrough. The process 10 also employs a quench blower 20 positioned adjacent the curtain of fibers extending from the spinneret 18. Air from the quench air blower 20 quenches the fibers extending from the spinneret 18. The quench air may be directed from one side of the fiber curtain as shown in FIG. 2 or both sides of the fiber curtain, or the air may be directed at the fibers radially from either the interior or exterior of the fibers. Alternatively, the fibers may be quenched by a medium other than air, such as water, water mists or other fluids.

To form a fiber with the desired length, the quenched fibers are generally melt drawn, such as using a fiber draw unit 22 as shown in FIG. 2. Fiber draw units or aspirators for use in melt spinning polymers are well-known in the art. Suitable fiber draw units for use in the process of the present invention include a linear fiber aspirator of the type shown in U.S. Pat. Nos. 3,802,817 and 3,423,255. The fiber draw 22 generally includes an elongated vertical passage through which the fibers are drawn by aspirating air entering from the sides of the passage and flowing downwardly through the passage. A heater or blower 24 supplies aspirating air to the fiber draw unit 22. The aspirating air melt draws the fibers and ambient air through the fiber draw unit 22. The flow of gas causes the fibers to melt draw or attenuate, which increases the molecular orientation or crystallinity of the polymers forming the fibers. When employing a fiber draw unit, the "draw down" ratio may be selected to help achieve the desired fiber length. The "drawn down" ratio is the linear speed of the fibers after drawing (e.g., linear speed of the godet roll 42 or a foraminous surface (not shown) divided by the linear speed of the fibers after extrusion). For example, the draw down ratio during melt drawing may be calculated as follows:

$$\text{Draw Down Ratio} = A/B$$

wherein,

A is the linear speed of the fiber after melt drawing (e.g., godet speed) and is directly measured; and B is the linear speed of the extruded fiber and can be calculated as follows:

$$\text{Extruder linear fiber speed} = C/(25 * \pi * D * E^2)$$

wherein,

C is the throughput through a single hole (grams per minute);

D is the melt density of the polymer (grams per cubic centimeter); and

E is the diameter of the orifice (in centimeters) through which the fiber is extruded. In certain embodiments, the draw down ratio may be from about 2:1 to about 4000:1, in some embodiments from about 5:1 to about 2000:1, and in some embodiments, from about 10:1 to about 1000:1 and in some embodiments from about 15:1 to about 800:1.

Once formed, the fibers may be deposited through the outlet opening of the fiber draw unit 22 and onto a godet roll 42. If desired, the fibers collected on the godet roll 42 may optionally be subjected to additional in line processing and/or converting steps (not shown) as will be understood by those skilled in the art. For example, fibers may be collected and thereafter crimped, texturized, and/or and cut to an average fiber length in the range of from about 3 to about 80 millimeters, in some embodiments from about 4 to about 65 millimeters, and in some embodiments, from about 5 to about 50 millimeters. The staple fibers may then be incorporated into a nonwoven web as is known in the art, such as bonded carded webs, through-air bonded webs, etc. The resulting fibers may then be annealed and drawn in their solid state to form the desired porous network.

The degree of drawing depends in part of the nature of the material being drawn (e.g., fiber, film, etc.). The composition is typically drawn (e.g., in the machine direction) to a draw ratio of from about 1.1 to about 25, in some embodiments from about 1.5 to about 15, and in some embodiments, from about 2 to about 10. The draw ratio may be determined by dividing the length of the drawn material by its length before drawing. The draw rate may also vary to help achieve the desired properties, such as within the range of from about 5% to about 1500% per minute of deformation, in some embodiments from about 20% to about 1000% per minute of deformation, and in some embodiments, from about 25% to about 850% per minute of deformation. Although the composition is typically drawn without the application of external heat (e.g., heated rolls), such heat might be optionally employed to improve processability, reduce draw force, increase draw rates, and improve fiber uniformity.

Drawing may occur in one or multiple stages. In FIG. 2, for instance, the fibers may be initially melt drawn by the fiber draw unit 22, transferred to a nip (not shown) where the polyester is allowed to cool below its melting temperature, and thereafter subjected to an additional drawing step before being deposited on the godet roll 42. In other cases, however, the fibers may be removed from the fiber forming machinery and subjected to an additional drawing step. Regardless, various drawing techniques may be employed, such as aspiration (e.g., fiber draw units), tensile frame drawing, biaxial drawing, multi-axial drawing, profile drawing, vacuum drawing, etc.

Drawing in the manner described above can result in the formation of pores that have a "nano-scale" cross-sectional dimension ("nanopores"), such as about 800 nanometers or less, in some embodiments from about 5 to about 700 nanometers, and in some embodiments, from about 10 to about 500 nanometers. The nanopores may also have an average axial dimension (e.g., length) of from about 100 to about 5000 nanometers, in some embodiments from about 50 to about 2000 nanometers, and in some embodiments, from about 100 to about 1000 nanometers. Micropores may also be formed during drawing that have an average cross-sectional dimension of about 0.2 micrometers or more, in some embodiments about 0.5 micrometers or more, and in some embodiments, from about 0.5 micrometers to about 5 micrometers. In certain cases, the axial dimension of the micropores and/or nanopores may be larger than the cross-sectional dimension so that the aspect ratio (the ratio of the axial dimension to the cross-sectional dimension) is from about 1 to about 30, in some embodiments from about 1.1 to about 15, and in some embodiments, from about 1.2 to about 5. For example, the axial dimension of the micropores may be 1 micrometer or more, in some embodiments about 1.5 micrometers or more, and in some embodiments, from about 2 to about 30 micrometers.

Regardless of their particular size, the pores (e.g., nanopores, micropores, or both) can be distributed in a substantially homogeneous fashion throughout the material. For example, the pores may be distributed in columns that are oriented in a direction generally perpendicular to the direction in which a stress is applied. These columns may be generally parallel to each other across the width of the material. Without intending to be limited by theory, it is believed that the presence of such a homogeneously distributed porous network can result in a high thermal resistance as well as good mechanical properties (e.g., energy dissipation under load and impact strength). This is in stark contrast to conventional techniques for creating pores that involve the use of blowing agents, which tend to result in an uncontrolled pore distribution and poor mechanical properties. In addition to forming a porous network, drawing can also significantly increase the axial dimension of certain of the discrete domains so that they have a generally linear, elongated shape. For example, the elongated micro-scale domains may have an average axial dimension that is about 10% or more, in some embodiments from about 20% to about 500%, and in some embodiments, from about 50% to about 250% greater than the axial dimension of the domains prior to drawing. The axial dimension (e.g., length) after drawing may, for instance, range from about 1 µm to about 400 µm, in some embodiments from about 5 µm to about 200 µm, and in some embodiments from about 10 µm to about 150 µm. The micro-scale domains may also be relatively thin and thus have a small cross-sectional dimension, such as from about 0.02 to about 20 micrometers, in some embodiments from about 0.1 to about 10 micrometers, and in some embodiments, from 0.4 to about 5 micrometers. This may result in an aspect ratio for the domains (the ratio of the axial dimension to a dimension orthogonal to the axial dimension) of from about 2 to about 150, in some embodiments from about 3 to about 100, and in some embodiments, from about 4 to about 50. Due to their small size, the nano-scale domains are not typically elongated in the same manner as the micro-scale domains. Thus, the nano-scale domains may retain an average axial dimension (e.g., length) of from about 1 to about 1000 nanometers, in some embodiments from about 5 to about 800 nanometers, in some embodiments from about 10 to about 500 nanometers, and in some embodiments from about 20 to about 200 nanometers.

The resulting polymeric material is not brittle and thus can deform upon the application of strain, rather than fracture. In this regard, the polymeric material of is capable of exhibiting good "peak elongation properties, i.e., the percent elongation at its peak load. For example, the material may exhibit a peak elongation of about 10% or more, in some embodiments about 20% or more, and in some embodiments, from about 40% to about 500%, such as determined in accordance with ASTM D638–14 at 23° C. Such elongations may be achieved for materials having a wide variety of average thicknesses (e.g., fiber diameter), such as those ranging from about 0.1 to about 50 micrometers, in some embodiments from about 1 to about 40 micrometers, in some embodiments from about 2 to about 25 micrometers, and in some embodiments, from about 5 to about 15 micrometers. While possessing the ability to extend under strain, the material can also be relatively strong. For example, the material may exhibit a peak tensile stress of from about 20 to about 600 Megapascals ("MPa"), in some embodiments from about 25 to about 450 MPa, and in some embodiments, from about 30 to about 350 MPa, such as determined in accordance with ASTM D638–14 at 23° C. When the material is in the form of fibers, another parameter that is indicative of the relative strength is "tenacity", which indicates the tensile strength of a fiber expressed as force per unit linear density. For example, the fibers may have a tenacity of from about 0.75 to about 10 grams-force ("gr") per denier, in some embodiments from about 1 to about 8 gr per denier, and in some embodiments, from about 1.5 to about 6 gr per denier. The denier of the fibers may vary depending on the desired application. Typically, the fibers are formed to have a denier per filament (i.e., the unit of linear density equal to the mass in grams per 9000 meters of fiber) of less than about 30, in some embodiments less than about 15, and in some embodiments, from about 0.5 to about 10.

Although by no means required, the polymeric material may be converted into a different form before being employed in a final article or product. When fibers are formed, for instance, they may be subsequently formed into a nonwoven web structure by randomly depositing the fibers onto a forming surface (optionally with the aid of a vacuum) and then bonding the resulting web using any known technique. The nonwoven web may be formed before or after the fibers are drawn. In certain embodiments, for instance, it may be desired to form a nonwoven web from a plurality of fibers, and thereafter draw the fibers by stretching the nonwoven web to the extent desired to form the porous network. In an alternative embodiment, an endless forming surface may simply be positioned below a fiber aspiration unit that draws the fibers to the desired extent before the web is formed.

Once formed, the nonwoven web may then be bonded using any conventional technique, such as with an adhesive or autogenously (e.g., fusion and/or self-adhesion of the fibers without an applied external adhesive). Autogenous bonding, for instance, may be achieved through contact of the fibers while they are semi-molten or tacky, or simply by blending a tackifying resin and/or solvent with the polymer used to form the fibers. Suitable autogenous bonding techniques may include ultrasonic bonding, thermal bonding, through-air bonding, calendar bonding, and so forth. For example, the web may be further bonded or embossed with a pattern by a thermo-mechanical process in which the web is passed between a heated smooth anvil roll and a heated pattern roll. The pattern roll may have any raised pattern which provides the desired web properties or appearance. Desirably, the pattern roll defines a raised pattern which defines a plurality of bond locations which define a bond area between about 2% and 30% of the total area of the roll. Exemplary bond patterns include, for instance, those described in U.S. Pat. No. 3,855,046 to Hansen et al., U.S. Pat. No. 5,620,779 to Levy et al., U.S. Pat. No. 5,962,112 to Haynes et al., U.S. Pat. No. 6,093,665 to Sayovitz et al., as well as U.S. Design Pat. No. 428,267 to Romano et al.; U.S. Pat. No. 390,708 to Brown; 418,305 to Zander, et al.; U.S. Past. No. 384,508 to Zander, et al.; 384,819 to Zander, et al.; 358,035 to Zander, et al.; and 315,990 to Blenke, et al. The pressure between the rolls may be from about 5 to about 2000 pounds per lineal inch. The pressure between the rolls and the temperature of the rolls is balanced to obtain desired web properties or appearance while maintaining cloth like properties. As is well known to those skilled in the art, the temperature and pressure required may vary depending upon many factors including but not limited to, pattern bond area, polymer properties, fiber properties and nonwoven properties.

In addition to spunbond webs, a variety of other nonwoven webs may also be formed from the thermoplastic composition in accordance with the present invention, such as meltblown webs, bonded carded webs, wet-laid webs, airlaid webs, coform webs, hydraulically entangled webs, etc. For example, the thermoplastic composition may be extruded through a plurality of fine die capillaries into a converging high velocity gas (e.g., air) streams that attenuate the fibers to reduce their diameter. Thereafter, the meltblown fibers are carried by the high velocity gas stream and are deposited on a collecting surface to form a web of randomly dispersed meltblown fibers. Alternatively, the polymer may be formed into a carded web by placing bales of fibers formed from the thermoplastic composition into a picker that separates the fibers. Next, the fibers are sent through a combing or carding unit that further breaks apart and aligns the fibers in the machine direction so as to form a machine direction-oriented fibrous nonwoven web. Once formed, the nonwoven web is typically stabilized by one or more known bonding techniques as described above to form a bonded carded web. Composites and/or laminates may also be formed from the fibers.

III. Articles

Due to its unique and beneficial properties, the resulting polymeric material of the present invention is well suited for use in a variety of different types of articles, such as an absorbent article, packaging film, barrier film, medical product (e.g., gown, surgical drape, facemask, head covering, surgical cap, shoe covering, sterilization wrap, warming blanket, heating pad, etc.), and so forth. For example, the polymeric material may be incorporated into an "absorbent article" that is capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, mitt wipe, and so forth; medical absorbent articles, such as garments, fenestration materials, underpads, bedpads, bandages, absorbent drapes, and medical wipes; food service wipers; clothing articles; pouches, and so forth. Materials and processes suitable for forming such articles are well known to those skilled in the art. Absorbent articles, for instance, typically include a substantially liquid-impermeable layer (e.g., outer cover), a liquid-permeable layer (e.g., bodyside liner, surge layer, etc.), and an absorbent core. In one embodiment, for example, the polymeric material may be in the form of a fibrous material (e.g., nonwoven web) and used to form an outer cover of an absorbent article. If desired, the nonwoven web may be laminated to a liquid-impermeable film that is either vapor-permeable or vapor-impermeable.

The polymeric material may likewise be in the form of a film that is used in an absorbent article, such as a liquid-impermeable film of the outer cover, which is either vapor-permeable or vapor-impermeable.

Absorbent articles, for instance, generally include an absorbent member (e.g., core layer, surge layer, transfer delay layer, wrapsheet, ventilation layer, etc.) positioned between a backsheet and a topsheet. The absorbent article may also contain other components as is known in the art, such as side panels, containment flaps, ears, waist or leg bands, etc. Generally speaking, the polymeric material of the present invention may be employed in any layer or component of the absorbent article, such as the topsheet, backsheet, and/or absorbent member. When employed in certain layers or components (e.g., backsheet), it may be desirable to laminate the polymeric material of the present invention to another layer (e.g., a film).

In this regard, various exemplary embodiments of the absorbent article will be described. Referring to FIG. 1, for instance, one particular embodiment of an absorbent article 201 is shown in the form of a diaper. However, as noted above, the invention may be embodied in other types of absorbent articles, such as incontinence articles, sanitary napkins, diaper pants, feminine napkins, training pants, and so forth. In the illustrated embodiment, the absorbent article 201 is shown as having an hourglass shape in an unfastened configuration. However, other shapes may of course be utilized, such as a generally rectangular shape, T-shape, or I-shape. As shown, the absorbent article 201 includes a chassis 202 formed by various components, including a backsheet 217, topsheet 205, and absorbent member that includes an absorbent core layer 203 and surge layer 207. It should be understood, however, that other layers may also be used in the present invention. Likewise, one or more of the layers referred to in FIG. 1 may also be eliminated in certain embodiments of the present invention.

As indicated above, the backsheet 217 may contain the polymeric material of the present invention. If desired, the nonwoven web may be positioned so that it defines a garment-facing surface 333 of the absorbent article 201. The absorbent article 201 also includes a topsheet 205. The topsheet 205 is generally designed to contact the body of the user and is liquid-permeable. For example, the topsheet 205 may define a body-facing surface 218, which is typically compliant, soft feeling, and non-irritating to the wearers skin. If desired, the topsheet 205 may contain the polymeric material (e.g., nonwoven web) of the present invention. For example, the nonwoven web may be positioned so that it defines the body-facing surface 218 if so desired. The topsheet may surround the absorbent core layer 203 so that it completely encases the absorbent article. Alternatively, the topsheet 205 and the backsheet 217 may extend beyond the absorbent member and be peripherally joined together, either entirely or partially, using known techniques, such as by adhesive bonding, ultrasonic bonding, etc. As indicated above, the topsheet 205 may include the polymeric material (e.g., nonwoven web) of the present invention. The topsheet 205 may also include a conventional a nonwoven web (e.g., spunbond web, meltblown web, or bonded carded web). Other exemplary topsheet constructions that contain a nonwoven web are described in U.S. Pat. Nos. 5,192,606; 5,702,377; 5,931,823; 6,060,638; and 6,150,002, as well as U.S. Patent Application Publication Nos. 2004/0102750, 2005/0054255, and 2005/0059941. The topsheet 205 may also contain a plurality of apertures formed therethrough to permit body fluid to pass more readily into the absorbent core layer 203. The apertures may be randomly or uniformly arranged throughout the topsheet 205, or they may be located only in the narrow longitudinal band or strip arranged along the longitudinal axis of the absorbent article. The apertures permit rapid penetration of body fluid down into the absorbent member. The size, shape, diameter and number of apertures may be varied to suit one's particular needs.

The absorbent article also contains an absorbent member positioned between the topsheet and the backsheet. The absorbent member may be formed from a single absorbent layer or a composite containing separate and distinct absorbent layer. It should be understood, however, that any number of absorbent layers may be utilized in the present invention. In FIG. 1, for instance, the absorbent member contains an absorbent core layer 203 and a surge layer 207 that helps to decelerate and diffuse surges or gushes of liquid that may be rapidly introduced into the absorbent core layer 203. Desirably, the surge layer 207 rapidly accepts and temporarily holds the liquid prior to releasing it into the storage or retention portions of the absorbent core layer 203. In the illustrated embodiment, for example, the surge layer 207 is interposed between an inwardly facing surface 216 of the topsheet 205 and the absorbent core layer 203. Alternatively, the surge layer 207 may be located on the outwardly facing surface 218 of the topsheet 205. The surge layer 207 is typically constructed from highly liquid-permeable materials. Suitable materials may include porous woven materials, porous nonwoven materials, and apertured films. In one embodiment, the surge layer 207 may contain the polymeric material of the present invention. Other examples of suitable surge layers are described in U.S. Pat. No. 5,486,166 to Ellis, et al. and U.S. Pat. No. 5,490,846 to Ellis, et al.

If desired, the absorbent member may also contain a transfer delay layer positioned vertically below the surge layer. The transfer delay layer may contain a material that is less hydrophilic than the other absorbent layers, and may generally be characterized as being substantially hydrophobic. For example, the transfer delay layer may be a polymeric material (e.g., nonwoven web) formed according to the present invention. The fibers may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay layer are described in U.S. Pat. No. 4,798,603 to Meyer, et al. and U.S. Pat. No. 5,248,309 to Serbiak, et al. To adjust the performance of the invention, the transfer delay layer may also be treated with a selected amount of surfactant to increase its initial wettability.

The transfer delay layer may generally have any size, such as a length of about 150 mm to about 300 mm. Typically, the length of the transfer delay layer is approximately equal to the length of the absorbent article. The transfer delay layer may also be equal in width to the surge layer, but is typically wider. For example, the width of the transfer delay layer may be from between about 50 mm to about 75 mm, and particularly about 48 mm. The transfer delay layer typically has a basis weight less than that of the other absorbent members. For example, the basis weight of the transfer delay layer is typically less than about 150 grams per square meter (gsm), and in some embodiments, between about 10 gsm to about 100 gsm. If desired, the transfer delay layer may contain the polymeric material (e.g., nonwoven web) of the present invention.

Besides the above-mentioned components, the absorbent article 201 may also contain various other components as is known in the art. For example, the absorbent article 201 may also contain a substantially hydrophilic wrapsheet (not illustrated) that helps maintain the integrity of the fibrous structure of the absorbent core layer 203. The wrapsheet is typically placed about the absorbent core layer 203 over at least the two major facing surfaces thereof, and composed of an absorbent cellulosic material, such as creped wadding or a high wet-strength tissue. The wrapsheet may be configured to provide a wicking layer that helps to rapidly distribute liquid over the mass of absorbent fibers of the absorbent core layer 203. The wrapsheet material on one side of the absorbent fibrous mass may be bonded to the wrapsheet located on the opposite side of the fibrous mass to effectively entrap the absorbent core layer 203. Furthermore, the absorbent article 201 may also include a ventilation layer (not shown) that is positioned between the absorbent core layer 203 and the backsheet 217. When utilized, the ventilation layer may help insulate the backsheet 217 from the absorbent core layer 203, thereby reducing dampness in the backsheet 217. Examples of such ventilation layers may include a nonwoven web laminated to a breathable film, such as described in U.S. Pat. No. 6,663,611 to Blaney, et al. If desired, the wrapsheet and/or ventilation layer may contain the polymeric material of the present invention.

In some embodiments, the absorbent article 201 may also include a pair of ears (not shown) that extend from the side edges 232 of the absorbent article 201 into one of the waist regions. The ears may be integrally formed with a selected diaper component. For example, the ears may be integrally formed with the backsheet 217 or from the material employed to provide the top surface, which may include the polymeric material of the present invention if so desired. In alternative configurations, the ears may be provided by members connected and assembled to the backsheet 217, the top surface, between the backsheet 217 and top surface, or in various other configurations. As noted above, the ears may contain the polymeric material of the present invention if so desired.

As representatively illustrated in FIG. 1, the absorbent article 201 may also include a pair of containment flaps 212 that are configured to provide a barrier and to contain the lateral flow of body exudates. The containment flaps 212 may be located along the laterally opposed side edges 232 of the topsheet 205 adjacent the side edges of the absorbent core layer 203. The containment flaps 212 may extend longitudinally along the entire length of the absorbent core layer 203, or may only extend partially along the length of the absorbent core layer 203. When the containment flaps 212 are shorter in length than the absorbent core layer 203, they may be selectively positioned anywhere along the side edges 232 of absorbent article 201 in a crotch region 210. In one embodiment, the containment flaps 212 extend along the entire length of the absorbent core layer 203 to better contain the body exudates. Such containment flaps 212 are generally well known to those skilled in the art. For example, suitable constructions and arrangements for the containment flaps 212 are described in U.S. Pat. No. 4,704,116 to Enloe. If desired, the containment flaps may contain the polymeric material of the present invention.

The absorbent article 201 may include various elastic or stretchable materials, such as a pair of leg elastic members 206 affixed to the side edges 232 to further prevent leakage of body exudates and to support the absorbent core layer 203. In addition, a pair of waist elastic members 208 may be affixed to longitudinally opposed waist edges 215 of the absorbent article 201. The leg elastic members 206 and the waist elastic members 208 are generally adapted to closely fit about the legs and waist of the wearer in use to maintain a positive, contacting relationship with the wearer and to effectively reduce or eliminate the leakage of body exudates from the absorbent article 201. The absorbent article 201 may also include one or more fasteners 230. For example, two flexible fasteners 130 are illustrated in FIG. 1 on opposite side edges of waist regions to create a waist opening and a pair of leg openings about the wearer. The shape of the fasteners 230 may generally vary, but may include, for instance, generally rectangular shapes, square shapes, circular shapes, triangular shapes, oval shapes, linear shapes, and so forth. The fasteners may include, for instance, a hook material. In one particular embodiment, each fastener 230 includes a separate piece of hook material affixed to the inside surface of a flexible backing. The elastic members (e.g., leg, waist, etc.) and/or fasteners may contain the polymeric material of the present invention if desired.

The various regions and/or components of the absorbent article 201 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the backsheet 217 and topsheet 205 are assembled to each other and to the absorbent core layer 203 using an adhesive. Alternatively, the absorbent core layer 203 may be connected to the backsheet 217 using conventional fasteners, such as buttons, hook and loop type fasteners, adhesive tape fasteners, and so forth. Similarly, other diaper components, such as the leg elastic members 206, waist elastic members 208 and fasteners 230, may also be assembled into the absorbent article 201 using any attachment mechanism.

Although various configurations of a diaper have been described above, it should be understood that other diaper and absorbent article configurations are also included within the scope of the present invention. In addition, the present invention is by no means limited to diapers. In fact, any other absorbent article may be formed in accordance with the present invention, including, but not limited to, other personal care absorbent articles, such as training pants, absorbent underpants, adult incontinence products, feminine hygiene products (e.g., sanitary napkins), swim wear, baby wipes, and so forth; medical absorbent articles, such as garments, fenestration materials, underpads, bandages, absorbent drapes, and medical wipes; food service wipers; clothing articles; and so forth.

The polymeric material may also be employed in a wide variety of other types of articles. Non-limiting examples include, for instance, insulation materials for refrigeration units (e.g., refrigerators, freezers, vending machines, etc.); automotive components (e.g., front and rear seats, headrests, armrests, door panels, rear shelves/package trays, steering wheels and interior trim, dashboards, etc.);

building panels and sections (e.g., roofs, wall cavities, under floors, etc.); apparel (e.g., coats, shirts, pants, gloves, aprons, coveralls, shoes, boots, headware, sock liners, etc.); furniture and bedding (e.g., sleeping bags, comforters, etc.); fluid storage/transfer systems (e.g., pipes or tankers for liquid/gas hydrocarbons, liquid nitrogen, oxygen, hydrogen, or crude oil); extreme environments (e.g., underwater or space); food and beverage products (e.g., cups, cup holders, plates, etc.); containers and bottles; industrial fabrics; insulation fabrics; and so forth. The polymeric material may also be used in a "garment", which is generally meant to include any article that is shaped to fit over a portion of a body. Examples of such articles include, without limitation, clothing (e.g., shirts, pants, jeans, slacks, skirts, coats, activewear, athletic, aerobic, and exercise apparel, swimwear, cycling jerseys or shorts, swimsuit/bathing suit, race suit, wetsuit, bodysuit, etc.), footwear (e.g., shoes, socks, boots, etc.), protective apparel (e.g., firefighter's coat), clothing accessories (e.g., belts, bra straps, side panels, gloves, hosiery, leggings, orthopedic braces, etc.), undergarments (e.g., underwear, t-shirts, etc.), compression garments, draped garments (e.g., kilts loincloths, togas, ponchos, cloaks, shawls, etc.), and so forth.

The present invention may be better understood with reference to the following examples.

Test Methods

Melt Flow Rate:

The melt flow rate ("MFR") is the weight of a polymer (in grams) forced through an extrusion rheometer orifice (0.0825-inch diameter) when subjected to a load of 2160 grams in 10 minutes, such as at 190° C., 210° C., 230° C., or 260° C. Unless otherwise indicated, melt flow rate is measured in accordance with ASTM Test Method D1238-13 with a Tinius Olsen Extrusion Plastometer.

Thermal Properties:

The glass transition temperature ($T_g$) may be determined by dynamic mechanical analysis (DMA) in accordance with ASTM E1640-13. A Q800 instrument from TA Instruments may be used. The experimental runs may be executed in tension/tension geometry, in a temperature sweep mode in the range from −120° C. to 150° C. with a heating rate of 3° C./min. The strain amplitude frequency may be kept constant (2 Hz) during the test. Three (3) independent samples may be tested to get an average glass transition temperature, which is defined by the peak value of the tan δ curve, wherein tan δ is defined as the ratio of the loss modulus to the storage modulus (tan δ=E"/E').

The melting temperature may be determined by differential scanning calorimetry (DSC). The differential scanning calorimeter may be a DSC Q100 Differential Scanning Calorimeter, which may be outfitted with a liquid nitrogen cooling accessory and with a UNIVERSAL ANALYSIS 2000 (version 4.6.6) analysis software program, both of which are available from T.A. Instruments Inc. of New Castle, Del. To avoid directly handling the samples, tweezers or other tools may be used. The samples may be placed into an aluminum pan and weighed to an accuracy of 0.01 milligram on an analytical balance. A lid may be crimped over the material sample onto the pan. Typically, the resin pellets may be placed directly in the weighing pan.

The differential scanning calorimeter may be calibrated using an indium metal standard and a baseline correction may be performed, as described in the operating manual for the differential scanning calorimeter. A material sample may be placed into the test chamber of the differential scanning calorimeter for testing, and an empty pan may be used as a reference. All testing may be run with a 55-cubic centimeter per minute nitrogen (industrial grade) purge on the test chamber. For resin pellet samples, the heating and cooling program is a 2-cycle test that began with an equilibration of the chamber to −30° C., followed by a first heating period at a heating rate of 10° C. per minute to a test temperature (e.g., 300° C.), followed by equilibration of the sample at the test temperature for 3 minutes, followed by a first cooling period at a cooling rate of 10° C. per minute to a temperature of −30° C., followed by equilibration of the sample at −30° C. for 3 minutes, and then a second heating period at a heating rate of 10° C. per minute to the test temperature. For fiber samples, the heating and cooling program may be a 1-cycle test that begins with an equilibration of the chamber to −25° C., followed by a heating period at a heating rate of 10° C. per minute to the test temperature, followed by equilibration of the sample at the test temperature for 3 minutes, and then a cooling period at a cooling rate of 10° C. per minute to a temperature of −30° C. All testing may be run with a 55-cubic centimeter per minute nitrogen (industrial grade) purge on the test chamber.

The results may be evaluated using the UNIVERSAL ANALYSIS 2000 analysis software program, which identifies and quantifies the glass transition temperature ($T_g$) of inflection, the endothermic and exothermic peaks, and the areas under the peaks on the DSC plots. The glass transition temperature may be identified as the region on the plot-line where a distinct change in slope occurred, and the melting temperature may be determined using an automatic inflection calculation.

Film Tensile Properties:

Films may be tested for tensile properties (peak stress, modulus, strain at break, and energy per volume at break) on a MTS Synergie 200 tensile frame. The test may be performed in accordance with ASTM D638-14 (at about 23° C.). Film samples may be cut into dog bone shapes with a center width of 3.0 mm before testing. The dog-bone film samples may be held in place using grips on the MTS Synergie 200 device with a gauge length of 18.0 mm. The film samples may be stretched at a crosshead speed of 5.0 in/min until breakage occurred. Five samples may be tested for each film in both the machine direction (MD) and the cross direction (CD). A computer program (e.g., TestWorks 4) may be used to collect data during testing and to generate a stress versus strain curve from which a number of properties may be determined, including modulus, peak stress, elongation, and energy to break.

Fiber Tensile Properties:

Fiber tensile properties may be determined in accordance with ASTM D638-14 at 23° C. For instance, individual fiber specimens may initially be shortened (e.g., cut with scissors) to 38 millimeters in length, and placed separately on a black velvet cloth. 10 to 15 fiber specimens may be collected in this manner. The fiber specimens may then be mounted in a substantially straight condition on a rectangular paper frame having external dimension of 51 millimeters x 51 millimeters and internal dimension of 25 millimeters×25 millimeters. The ends of each fiber specimen may be operatively attached to the frame by carefully securing the fiber ends to the sides of the frame with adhesive tape. Each fiber specimen may be measured for its external, relatively shorter, cross-fiber dimension employing a conventional laboratory microscope, which may be properly calibrated and set at 40× magnification. This cross-fiber dimension may be recorded as the diameter of the individual fiber specimen. The frame helps to mount the ends of the sample fiber specimens in the upper and lower grips of a constant rate of extension type tensile tester in a manner that avoids excessive damage to the fiber specimens.

A constant rate of extension type of tensile tester and an appropriate load cell may be employed for the testing. The load cell may be chosen (e.g., 10N) so that the test value falls within 10–90% of the full scale load. The tensile tester (i.e., MTS SYNERGY 200) and load cell may be obtained from MTS Systems Corporation of Eden Prairie, Mich. The fiber specimens in the frame assembly may then be mounted between the grips of the tensile tester such that the ends of the fibers may be operatively held by the grips of the tensile tester. Then, the sides of the paper frame that extend parallel to the fiber length may be cut or otherwise separated so that the tensile tester applies the test force only to the fibers. The fibers may be subjected to a pull test at a pull rate and grip speed of 12 inches per minute. The resulting data may be analyzed using a TESTWORKS 4 software program from the MTS Corporation with the following test settings:

| Calculation Inputs | | Test Inputs | |
|---|---|---|---|
| Break mark drop | 50% | Break sensitivity | 90% |
| Break marker elongation | 0.1 in | Break threshold | 10 $g_f$ |
| Nominal gage length | 1 in | Data Acq. Rate | 10 Hz |
| Slack pre-load | 1 $lb_f$ | Denier length | 9000 m |
| Slope segment length | 20% | Density | 1.4 g/cm³ (PET) or 1.25 (PLA) |
| Yield offset | 0.20% | Initial speed | 12 in/min |
| Yield segment length | 2% | Secondary speed | 2 in/min |

The tenacity values may be expressed in terms of gram-force per denier. Peak elongation (% strain at break) and peak stress may also be measured.

Expansion Ratio, Density, and Percent Pore Volume

To determine expansion ratio, density, and percent pore volume, the width ($W_i$) and thickness ($T_i$) of the specimen may be initially measured prior to drawing. The length ($L_i$) before drawing may also be determined by measuring the distance between two markings on a surface of the specimen. Thereafter, the specimen may be drawn to initiate voiding. The width ($W_f$), thickness ($T_f$), and length ($L_f$) of the specimen may then be measured to the nearest 0.01 mm utilizing Digimatic Caliper (Mitutoyo Corporation). The volume (V) before drawing may be calculated by $W_i \times T_i \times L_i = V_i$. The volume ($V_f$) after drawing may also be calculated by $W_f \times T_f \times L_f = V_f$. The expansion ratio ($\phi$) may be calculated by $\phi = V_f/V_i$; the density ($P_f$) may be calculated by: $P_f = P_i/\phi$, where $P_i$ is density of precursor material; and the percent pore volume ($V_v$) may be calculated by: $\%V_v = (1-1/\phi) \times 100$.

For fibers, the void content may also be measured by suspension in calibrated density solutions. For example, density solutions can be produced by mixing sodium bromide (Sigma-Aldrich) with deionized water to create solutions with densities ranging from 1.0 gram per cubic centimeter (g/cc) to 1.385 g/cc. The solution density may be verified using calibrated hygrometers obtained from VWR.

EXAMPLE 1

A blend of 93 wt. % semi-crystalline polyethylene terephthalate (PET 7200 Auriga) and 7 wt. % polyester-polyether copolymer (HYTREL™ RS 40F3 NC010, DuPont). The polymers were fed into a co-rotating, twin-screw extruder (ZSK-30, diameter of 30 mm, length of 1328 millimeters) for compounding that was manufactured by Werner and Pfleiderer Corporation of Ramsey, N.J.

The extruder possessed 14 zones, numbered consecutively 1–14 from the feed hopper to the die. The first barrel zone #1 received the resins via gravimetric feeder at a total throughput of 20 pounds per hour. The die used to extrude the resin had 3 die openings (6 millimeters in diameter) that were separated by 4 millimeters. Upon formation, the extruded resin was cooled on a fan-cooled conveyor belt and formed into pellets by a Conair pelletizer. The extruder screw speed was 200 revolutions per minute ("rpm") and the extrusion temperature was 270° C. The resulting pellets were dried via a desiccant drying at 140° C. for 12 hours.

EXAMPLE 2

The pellets of EXAMPLE 1 were then extruded as a monocomponent fiber using a multifilament fiber spinning line (FET-100 Series Laboratory Multi-Functional Melt Spinning System) manufactured by Fibre Extrusion Technologies, Leeds UK. Pellets were flood fed into signal screw extruder heated to a temperature of 275° C. The melted polymer was then extruded through a fiber spinneret with 24 holes measuring 0.15 mm in diameter with a capillary length of 0.6 mm at a throughput of 0.39 grams per hole per minute. The fiber was melt drawn via a godet roll at 200 meters per minute. The total fiber bundle denier was approximately 485 grams per 9000 meters.

EXAMPLE 3

The fiber bundle of EXAMPLE 2 was fed into a draw line via a quintet roller stand at infeed speed of 10 meters per minute (mpm). The bundle then traversed around two bars submerged in water bath having diameter of 19 mm. The two bars were located at approximately 87 centimeters from the water bath entrance and fixed at a position yielding a 180-degree wrap before exiting the water bath. The water bath temperature was 25° C. The bundle take-up speed was 40 meters per minute giving a draw ratio of 4.0×. Limited breaks in the fibers were observed.

EXAMPLE 4

Fibers were formed as in EXAMPLE 3 except the take-up speed was 42 meters per minute giving a draw ratio of 4.2×. Limited breaks in the fibers were observed.

EXAMPLE 5

Fibers were formed as in EXAMPLE 3 but the take up speed was 45 meters per minute giving a draw ratio of 4.5×. Limited breaks in the fibers were observed.

EXAMPLE 6

Fibers were formed as in EXAMPLE 3, however the water was removed from the water bath. A medium level of breaks in the fibers were observed.

EXAMPLE 7

The pellets of EXAMPLE 1 were then extruded as a monocomponent fiber using a multifilament fiber spinning line manufactured by Davis Standard, Pawcatuck, Conn., USA. Pellets were flood fed into signal screw extruder heated to a temperature of 275° C. The melted polymer was then extruded through a fiber spinneret with 48 holes measuring 0.30 mm in diameter with a capillary length of 0.6 mm at a throughput of 0.3 grams per hole per minute. The fiber was collected at a godet take-up speed of 50 mpm for a draw down ratio of 14.5. The total bundle denier was approximately 2544 grams per 9000 meters. The bundle was wrapped on a grip and subjected to uniaxial extension under MTS hydraulic frame (810 Material Test System) at ambient condition. The gage length was 15 mm and the bundle extension speed was 50 meters per minute with a draw ratio of approximately 3×. Limited breaks in the fibers were observed.

EXAMPLE 8

Fibers were formed as in EXAMPLE 6 but the bundle extension speed was 100 meters per minute. A medium level of breaks in the fibers were observed.

EXAMPLE 9

The pellets of EXAMPLE 1 were then extruded as a monocomponent fiber using a multifilament fiber spinning line manufactured by Davis Standard, Pawcatuck, Conn., USA. Pellets were flood fed into signal screw extruder heated to a temperature of 275° C. The melted polymer was then extruded through a fiber spinneret with 48 holes measuring 0.30 mm in diameter with a capillary length of 0.6 mm at a throughput of 0.3 grams per hole per minute. The fiber was collected at a godet take-up speed of 100 mpm for a draw down ratio of 29. 1632 grams per 9000 meters. The bundle was wrapped on a grip and subjected to uniaxial extension under MTS hydraulic frame (810 Material Test System) at ambient condition. The gage length was 15 mm and the bundle extension speed was 50 meters per minute with a draw ratio of approximately 3X. Limited breaks in the fibers were observed.

EXAMPLE 10

A blend of 93 wt. % semi-crystalline polyethylene terephthalate (PET 7200 Auriga) and 7 wt. % polyester-polyether copolymer (HYTREL™ 5526, DuPont). The polymers were fed into a co-rotating, twin-screw extruder (ZSK-30, diameter of 30 mm, length of 1328 millimeters) for compounding that was manufactured by Werner and Pfleiderer Corporation of Ramsey, N.J. The extruder possessed 14 zones, numbered consecutively 1-14 from the feed hopper to the die. The first barrel zone #1 received the resins via gravimetric feeder at a total throughput of 20 pounds per hour. The die used to extrude the resin had 3 die openings (6 millimeters in diameter) that were separated by 4 millimeters. Upon formation, the extruded resin was cooled on a fan-cooled conveyor belt and formed into pellets by a Conair pelletizer. The extruder screw speed was 200 revolutions per minute ("rpm") and the extrusion temperature was 270° C. The resulting pellets were dried via a desiccant drying at 140° C. for 12 hours.

EXAMPLE 11

The pellets of EXAMPLE 10 were then extruded as a monocomponent fiber using a multifilament fiber spinning line (FET-100 Series Laboratory Multi-Functional Melt Spinning System) manufactured by Fibre Extrusion Technologies, Leeds UK. Pellets were flood fed into signal screw extruder heated to a temperature of 275° C. The melted polymer was then extruded through a fiber spinneret with 24 holes measuring 0.15 mm in diameter with a capillary length of 0.3 mm at a throughput of 0.39 grams per hole per minute. The fibers were melt drawn using a godet roll with a take-up speed of 100 meters per minute for a draw down ratio of 5. The total bundle denier was approximately 886 grams per 9000 meters.

EXAMPLE 12

The fiber bundle from EXAMPLE 11 was fed into a draw line via quintet roller stand at feed speed of 10 meters per minute (mpm). The bundle then traversed through two bars submerged in water bath having length of 150 centimeters. The two bars were located at approximately 129 centimeters from the water bath entrance. The bundle traversed through the bars such that the bundle followed a 180-degree turn (s-wrap) before exiting the water bath. The water bath temperature was 25° C. The bundle take-up speed was 35 meters per minute giving a draw ratio of 3.5x. Limited breaks in the fibers were observed.

EXAMPLE 13

Fibers were formed as in EXAMPLE 12 except water was removed from the water bath. A medium level of breaks in the fibers were observed.

EXAMPLE 14

Pellets from EXAMPLE 10 were used to create the core of a bicomponent fibers) with the sheath made from of 100 wt. % polyethylene terephthalate (PET 7200 Auriga). The melted polymer was extruded through a spinneret with 24 holes measuring 0.40 mm in diameter with a capillary length of 1.6 mm at a throughput of 1.04 grams per hole per minute. The fibers were melt drawn using a godet roll with a take-up speed of 100 meters per minute for a draw down ratio of 14. The total bundle denier was approximately 2252 grams per 9000 meters.

Density and void measurements were also taken for the samples of Example 14, as well as Example 2 and 11. The results are set forth in the table below.

| | PET standard Density (g/cm³) | Measured Density (g/cm³) | Difference | Void Content |
|---|---|---|---|---|
| EXAMPLE 2 | 1.350 | 1.142 | 0.208 | 15.4% |
| EXAMPLE 11 | 1.350 | 1.055 | 0.295 | 21.8% |
| EXAMPLE 14 | 1.350 | 0.870 | 0.480 | 35.5% |

EXAMPLE 15

The fiber bundle of EXAMPLE 14 was feed into a draw line via quintet roller stand at feed speed of 10 meters per minute (mpm). The bundle then traversed through two bars submerged in water bath having length of 150 centimeters. The two bars were located at approximately 129 centimeters from the water bath entrance. The bundle traversed through the bars such that the bundle followed a 180-degree turn (s-wrap) before exiting the water bath. The water bath temperature was 25° C. The bundle take-up speed was 35 meters per minute giving a draw ratio of 3.5x. Limited breaks in the fibers were observed.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A polymeric material in the form of a film, fiber, or molded article, wherein the polymeric material comprises a thermoplastic composition, the composition containing a continuous phase that contains a polyester, wherein a copolyetherester elastomer is dispersed within the continuous phase in the form of discrete domains and wherein the copolyetherester elastomer is present in the thermoplastic composition in an amount of from about 0.01 wt. % to about 15 wt. %, and wherein a porous network is defined within the thermoplastic composition that includes a plurality of nanopores, wherein the nanopores are distributed homogenously throughout the polymeric material.

2. The polymeric material of claim 1, wherein the copolyetherester elastomer constitutes from about 0.05 wt. % to about 10 wt. % of the thermoplastic composition.

3. The polymeric material of claim 1, wherein the polyester is polylactic acid.

4. The polymeric material of claim 1, wherein the polyester is an aromatic polyester.

5. The polymeric material of claim 4, wherein the aromatic polyester is polyethylene terephthalate.

6. The polymeric material of claim 1, wherein the polyester has a glass transition temperature of about 0° C. or more.

7. The polymeric material of claim 1, wherein the copolyetherester elastomer is a segmented block copolymer that has recurring long chain ester units and short chain ester units.

8. The polymeric material of claim 7, wherein the long chain units are represented by the formula:

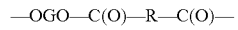

and the short chain ester units are represented by the structure:

—ODO—C(O)—R—C(O)— wherein,
G is a divalent group that is derived from one or more high molecular weight alcohols;
R is a hydrocarbon group derived from one or more dicarboxylic acids; and
D is a divalent group derived from one or more low molecular weight diols.

9. The polymeric material of claim 7, wherein the long chain units are formed from the reaction product of a high molecular weight alcohol with a dicarboxylic acid.

10. The polymeric material of claim 9, wherein the alcohol is a polymeric glycol.

11. The polymeric material of claim 7, wherein the short chain ester units are formed from the reaction of a low molecular weight diol with a dicarboxylic acid.

12. The polymeric material of claim 11, wherein the low molecular weight diol includes ethylene glycol, propylene glycol, 1,4-butanediol, 1,6-hexamethylene glycol, dihydroxycyclohexane, cyclohexane dimethanol, resorcinol, hydroquinone, 1,5-dihydroxynaphthalene, bisphenol A, or an ester derivative thereof.

13. The polymeric material of claim 8, wherein the dicarboxylic acid includes an aromatic dicarboxylic acid.

14. The polymeric material of claim 1, wherein the nanopores have an average cross-sectional dimension of about 800 nanometers or less.

15. The polymeric material of claim 1, wherein nanopores have an average axial dimension of from about 100 to about 5000 nanometers.

16. The polymeric material of claim 1, wherein the continuous phase constitutes from about 60 wt. % to about 99 wt. % of the thermoplastic composition.

17. The polymeric material of claim 1, wherein the copolyetherester elastomer is dispersed in the form of nanoscale domains.

18. The polymeric material of claim 1, wherein the composition further comprises a microinclusion additive dispersed within the continuous phase in the form of discrete domains.

19. The polymeric material of claim 1, wherein the porous network further includes micropores.

20. A fiber comprising the polymeric material of claim 1.

21. A nonwoven web comprising the fiber of claim 20.

22. An absorbent article that includes a substantially liquid-impermeable layer, liquid-permeable layer, and an absorbent core, wherein the substantially liquid-impermeable layer, the liquid-permeable layer, or both include the polymeric material of claim 1.

23. A method for forming a polymeric material in the form of a fiber, film, or molded article, the method comprising:
forming a thermoplastic composition that contains a continuous phase that includes a polyester and a copolyetherester elastomer that is dispersed within the continuous phase in the form of discrete domains wherein the copolyetherester elastomer is present in the thermoplastic composition in an amount of from about 0.01 wt. % to about 15 wt. %; and
solid state drawing the thermoplastic composition to form a porous network therein, the porous network including a plurality of nanopores, wherein the nanopores are distributed homogenously throughout the polymeric material.

24. The method of claim 23, wherein the thermoplastic composition is drawn to a stretch ratio of from about 1.1 to about 25.

25. The method of claim 23, wherein the thermoplastic composition is drawn at a temperature of from about −50° C. to about 150° C.

26. A method for forming a fiber, the method comprising:
forming a thermoplastic composition that contains a continuous phase that includes a polyester and a copolyetherester elastomer that is dispersed within the continuous phase in the form of discrete domains wherein the copolyetherester elastomer is present in the thermoplastic composition in an amount of from about 0.01 wt. % to about 15 wt. %;
extruding the composition through a capillary to form the fiber; and
drawing the fiber at a temperature that is lower than the melting temperature of the polyester, thereby forming a porous network that includes a plurality of nanopores, wherein the nanopores are distributed homogenously throughout the fiber.

* * * * *